US00PP13743P29

(12) United States Plant Patent
Klemm

(10) Patent No.: US PP13,743 P2
(45) Date of Patent: Apr. 29, 2003

(54) GERANIUM PLANT NAMED 'KLEP01012'

(75) Inventor: Nils Klemm, Stuttgart (DE)

(73) Assignee: Klemm & Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 10/171,837

(22) Filed: Jun. 17, 2002

(51) Int. Cl.[7] ..... A01H 5/00

(52) U.S. Cl. ..... Plt./325

(58) Field of Search ..... Plt./325, 328

*Primary Examiner*—Kent Bell
(74) *Attorney, Agent, or Firm*—C. A. Whealy

(57) ABSTRACT

A new and distinct cultivar of Zonal Geranium plant named 'KLEP01012', characterized by its uniform, compact and upright plant habit; dark green-colored leaves; freely flowering habit; purple and light pink bi-colored flowers; and upright and strong greenish brown peduncles.

1 Drawing Sheet

BOTANICAL CLASSIFICATION/CULTIVAR DESIGNATION

*Pelargonium×hortorum* cultivar 'KLEP01012'.

BACKGROUND OF THE INVENTION

The present invention relates to a new and distinct cultivar of Zonal Geranium plant, botanically known as *Pelargonium×hortorum,* and hereinafter referred to by the name 'KLEP01012'.

The new Zonal Geranium is a product of a planned breeding program conducted by the Inventor in Stuttgart, Germany. The objective of the breeding program was to develop new Zonal Geraniums with uniform and compact plant habit, large flowers, and interesting flower and foliage colors.

The new Zonal Geranium originated from a cross made by the Inventor in 1997 of a proprietary selection of *Pelargonium×hortorum* identified as CK 100, not patented, as the female, or seed, parent with a proprietary selection of *Pelargonium×hortorum* identified as MG 015, not patented, as the male, or pollen, parent. The cultivar KLEP01012 was discovered and selected by the Inventor as a flowering plant within the progeny from this cross in a controlled environment in Stuttgart, Germany, in 1997.

Asexual reproduction of the new cultivar by terminal cuttings taken at Stuttgart, Germany has shown that the unique features of this new Zonal Geranium are stable and reproduced true to type in successive generations of asexual reproduction.

SUMMARY OF THE INVENTION

The following traits have been repeatedly observed and are determined to be the unique characteristics of 'KLEP01012'. These characteristics in combination distinguish 'KLEP01012' as a new cultivar and distinguish it from other known Zonal Geranium cultivars:

1. Uniform, compact and upright plant habit.
2. Dark green-colored leaves.
3. Freely flowering habit.
4. Purple and light pink bi-colored flowers.
5. Upright and strong greenish brown peduncles.

Plants of the new Zonal Geranium differ primarily from plants of the female parent, the selection CK 100, in the following characteristics:

1. Plants of the new Zonal Geranium are more compact than plants of the selection CK 100.
2. Plants of the new Zonal Geranium have purple and light pink bi-colored flowers whereas plants of the selection CK 100 have dark pink-colored flowers.

Plants of the new Zonal Geranium differ primarily from plants of the male parent, the selection MG 015, in the following characteristics:

1. Plants of the new Zonal Geranium are not as compact as plants of the selection MG 015.
2. Plants of the new Zonal Geranium have purple and light pink bi-colored flowers whereas plants of the selection MG 015 have lavender pink-colored flowers.

The new Zonal Geranium can be compared to plants of the cultivar 'Klekit', disclosed in co-pending U.S. Plant Patent application Ser. No. 09/250,018. However, in side-by-side comparisons conducted in Stuttgart, Germany, plants of the new Zonal Geranium differed from plants of the cultivar Klekit in the following characteristics:

1. Leaves of the new Zonal Geranium did not have a distinct zonation pattern whereas leaves of the cultivar Klekit had a distinct zonation pattern.
2. Flowers of the new Zonal Geranium were purple and light pink bi-colored whereas flowers of the cultivar Klekit were purple and pink bi-colored.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description which accurately describe the colors of the new Zonal Geranium. The photograph comprises a side perspective view of a typical flowering plant of 'KLEP01012' grown in a 10-cm container.

DETAILED BOTANICAL DESCRIPTION

The cultivar KLEP01012 has not been observed under all possible environmental conditions. The phenotype may vary somewhat with variations in environment, such as temperature and light intensity, without, however, any variance in genotype.

The aforementioned photographs, following observations, and averaged measurements describe plants that were planted in January in 10-cm pots in Stuttgart, Germany, pinched one time about two weeks after planting, and grown for about three months under commercial practice in a glass-covered greenhouse with day temperatures about 18 to 22° C., night temperatures about 14 to 17° C., and light levels about 20,000 to 55,000 lux. Plants used for the photographs and detailed botanical description were about 88 days old.

In the following description, color references are made to The Royal Horticultural Society Colour Chart except where general terms of ordinary dictionary significance are used.

Botanical classification: *Pelargonium×hortorum* cultivar KLEP01012.

Parentage:

*Female parent.*—Proprietary selection of *Pelargonium×hortorum* identified as CK 100, not patented.

*Male parent.*—Proprietary selection of *Pelargonium×hortorum* identified as MG 015, not patented.

Propagation:

*Type cutting.*—Terminal cuttings.

*Time to initiate roots.*—Summer: About 10 days at 20° C. Winter: About 12 days at 20° C.

*Time to develop roots.*—Summer: About 18 days at 20° C. Winter: About 20 days at 20° C.

*Root description.*—Fine, freely branching, and white in color.

Plant description:

*General appearance.*—Uniform, compact and upright plant habit; densely foliated.

*Crop time.*—About three months are required to produce a finished flowering plant in 10 or 12-cm containers.

*Growth and branching habit.*—Moderately vigorous. Moderate basal branching, about three or four lateral branches develop without pinching, that is, removal of terminal apices.

*Plant height* (*to top of flower umbels*).—About 21 cm.

*Plant height* (*to top of foliar plane*).—About 15 cm.

*Plant width.*—About 22.5 cm.

*Lateral branches.*—Length: About 8 cm. Internode length: About 1.75 cm. Texture: Smooth. Color: 137C.

*Foliage description.*—Arrangement: Alternate, simple. Quantity of leaves per lateral branch: About 6 or 7. Length: About 6 cm. Width: About 8 cm. Shape: Round. Apex: Rounded. Base: Lobed, overlapping. Margin: Crenate. Venation pattern: Palmate. Texture, upper and lower surfaces: Rough. Color: Young and fully expanded foliage, upper surface: 137A; no distinct zonation pattern. Young and fully expanded foliage, lower surface: 137B. Venation, upper and lower surfaces: 138A. Petiole: Length: About 6 cm. Diameter: About 5 mm. Color, upper and lower surfaces: 137B.

Flower description:

*Flower arrangement.*—Purple and light pink bi-colored flowers arranged in rounded hemispherical umbels arising from apical leaf axils. Umbels displayed above the foliage on upright peduncles. Flowers semi-double in form, rounded and cup-shaped. Umbels persistent, flowers not persistent. Flowers not fragrant.

*Quantity of flowers.*—Freely flowering. At full flower, plants have about 3 to 5 open umbels and about 3 developing umbels and each umbel has about 18 to 25 flowers and flower buds.

*Flowering season.*—Year-round under greenhouse conditions. In the garden, flowering is continuous from spring until fall.

*Flower longevity.*—Flowers last about 8 days on the plant.

*Umbel size.*—Height: About 10 cm. Diameter: About 6 to 10 cm.

*Flower size.*—Diameter: About 4.5 cm. Depth (height): About 1 cm.

*Flower buds.*—Length: About 1.2 cm. Diameter: About 6.5 mm. Shape: Elliptic. Color: 139B.

*Petals.*—Quantity per flower: About 6 to 9. Length: About 2.5 cm. Width: About 2 cm. Shape: Ovate to round. Apex: Rounded. Base: Attenuate. Margin: Entire. Texture, upper and lower surfaces: Smooth, velvety. Color: When opening and fully opened, upper surface: 66A to 66B; towards apex, 69C; towards base, close to 155D; color does not fade with subsequent development. When opening and fully opened, lower surface: 73D. Venation, upper surface: 66A. Venation, lower surface: 66B.

*Petaloids.*—Quantity per flower: About 1 to 5. Length: About 3 to 10 mm; irregular in size. Width: About 1 to 5 mm; irregular in size. Shape: Variable, irregular. Apex: Mostly rounded. Base: Attenuate. Margin: Mostly entire. Texture, upper and lower surfaces: Smooth, velvety. Color: When opening and fully opened, upper surface: 66A to 67C; towards apex, 69C; color does not fade with subsequent development. When opening and fully opened, lower surface: 66A to 67C; towards apex, 69C. Venation, upper and lower surfaces: 66B.

*Sepals.*—Quantity per flower: Five, arranged in a single whorl. Length: About 9 mm. Width: About 4 mm. Shape: Elliptic. Apex: Narrowly acute. Margin: Entire. Texture, upper and lower surfaces: Pubescent, velvety. Color, upper and lower surfaces: 139C.

*Peduncle* (*umbel stem*).—Length: About 12.5 cm. Diameter: About 5 mm. Angle: Erect. Strength: Strong. Texture: Smooth. Color: 139C overlain with 174A.

*Pedicel* (*individual flower stem*).—Length: About 3 cm. Diameter: About 1.5 mm. Angle: Erect. Strength: Moderately strong. Texture: Rough. Color: 148A to 148B overlain with 175A to 176A.

*Reproductive organs.*—Androecium: Anther quantity per flower: About five. Anther length: About 3 mm. Anther shape: Ovate. Anther color: 32C. Pollen amount: Moderate. Pollen color: 32A. Gynoecium: Pistil quantity per flower: One. Pistil length: About 6 mm. Stigma shape: Five-parted, star-shaped. Stigma color: 57C. Style length: About 4 mm. Style color: 157D. Ovary color: 149D.

*Seed.*—Length: About 3 to 6 mm. Diameter: About 1.5 to 2 mm. Shape: Ovoid. Color: Brown.

Disease tolerance: Plants of the new Zonal Geranium have been observed to be tolerant to pathogens common to Pelargonium, such as Botrytis.

Weather tolerance: Plants of the new Zonal Geranium have been observed to tolerate rain, wind, and temperatures from 8 to 35° C.

It is claimed:

1. A new and distinct cultivar of Zonal Geranium plant named 'KLEP01012', as herein illustrated and described.

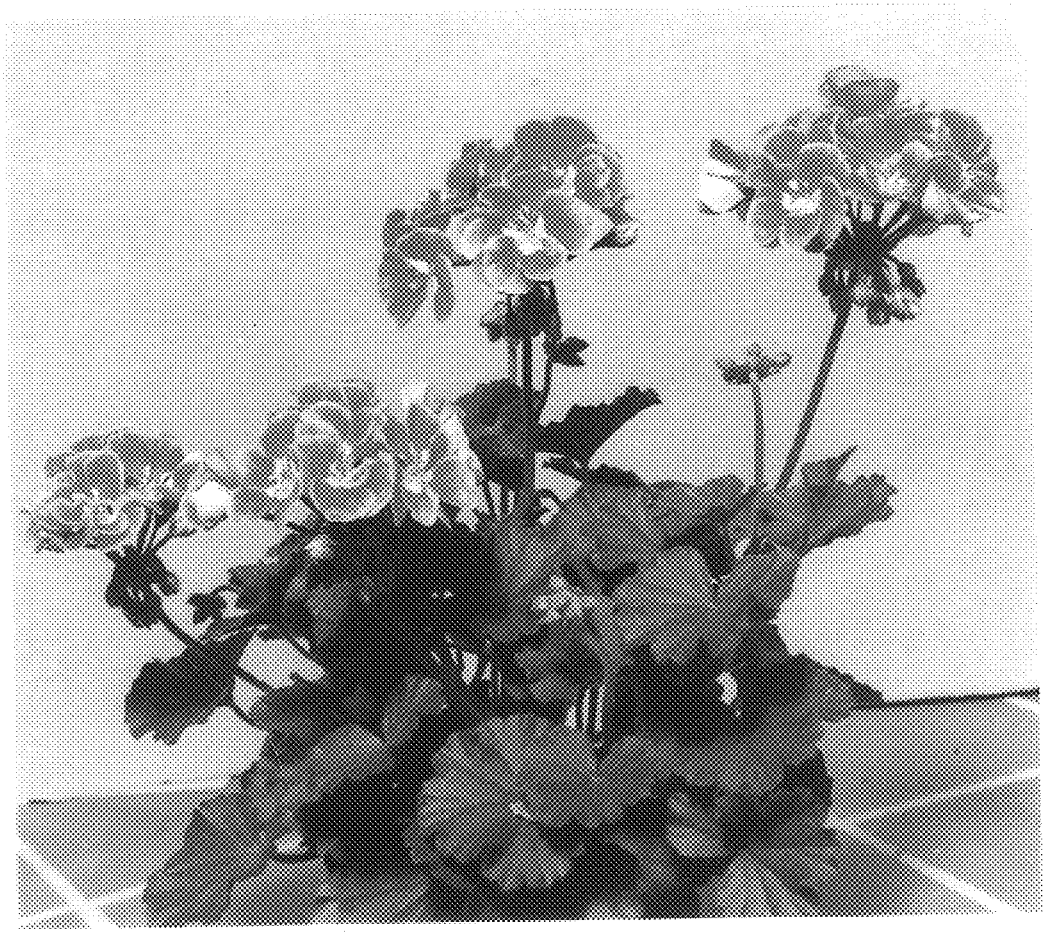

* * * * *